US009759693B2

United States Patent
Corcos et al.

(10) Patent No.: US 9,759,693 B2
(45) Date of Patent: Sep. 12, 2017

(54) METHOD OF SIMULATING THE ABSORPTION OF PLANE WAVES USING FEM SOFTWARE TOOLS

(71) Applicant: International Business Machines Corporation, Armonk, NY (US)

(72) Inventors: Dan Corcos, Nesher (IL); Danny Elad, Moshav Liman (IL); Noam Kaminski, Kiryat Tivon (IL); Bernhard Klein, Zürich (SZ); Lukas Kull, Zürich (SZ); Thomas Morf, Gross (SZ)

(73) Assignee: International Business Machines Corporation, Armonk, NY (US)

( * ) Notice: Subject to any disclaimer, the term of this patent is extended or adjusted under 35 U.S.C. 154(b) by 1148 days.

(21) Appl. No.: 13/721,088

(22) Filed: Dec. 20, 2012

(65) Prior Publication Data

US 2014/0180604 A1 Jun. 26, 2014

(51) Int. Cl.
*G01J 5/20* (2006.01)
*G01N 30/00* (2006.01)
*G01J 5/08* (2006.01)

(52) U.S. Cl.
CPC .......... *G01N 30/00* (2013.01); *G01J 5/0837* (2013.01); *G01J 5/20* (2013.01)

(58) Field of Classification Search
CPC .......... G01N 30/00; G01J 5/20; G01J 5/0837
See application file for complete search history.

(56) References Cited

U.S. PATENT DOCUMENTS 6,767,128 B1 * 7/2004 Daulle .................. G01R 21/02
374/120
6,958,853 B1 * 10/2005 Arnone ................. B82Y 20/00
359/326

(Continued)

FOREIGN PATENT DOCUMENTS

WO 2011151756 12/2011

OTHER PUBLICATIONS

Nguyen, D-T et al., "Broadband THz Uncooled Antenna-Coupled Microbolometer Array—Electromagnetic Design, Simulations and Measurements" (May 8, 2012), IEEE Transactions on Terahertz Science and Technology, vol. 2 No. 3, May 2012, p. 299-301.*

(Continued)

*Primary Examiner* — Aniss Chad
*Assistant Examiner* — Steven Crabb (57) ABSTRACT

A novel and useful method of visualization by detection of EM radiation being irradiated or reflected from objects in the imager's field of view using Finite Element Method (FEM) simulation software tools. The methodology provides a verification method of antenna operation from an electrical point of view since bolometer performance cannot be estimated using regular antenna parameters such as directivity, gain, impedance matching, etc. as the bolometer does not behave as an antenna but rather behaves as an absorber. An incident wave is triggered on the absorber and the absorption of the bolometer structure is estimated using commercially available Finite Element Method (FEM) software (e.g., ANSYS® HFSS software, CST MICROWAVE STUDIO®, etc.). How much of the energy is reflected is subsequently measured. The energy which is not reflected is considered to be absorbed by the absorber.

24 Claims, 7 Drawing Sheets

(56) References Cited

U.S. PATENT DOCUMENTS

| | | | | |
|---|---|---|---|---|
| 7,085,592 | B1* | 8/2006 | Davies | H01Q 3/08 343/703 |
| 2004/0087342 | A1* | 5/2004 | Fuenfgeld | G01S 7/03 455/562.1 |
| 2004/0102694 | A1* | 5/2004 | Iyama | G01R 29/08 600/410 |
| 2004/0252065 | A1* | 12/2004 | Agnese | G01J 5/08 343/703 |
| 2005/0276312 | A1* | 12/2005 | Yamaguchi | H04B 17/0085 375/144 |
| 2006/0017630 | A1* | 1/2006 | Kildal | G01R 29/105 343/703 |
| 2006/0231761 | A1 | 10/2006 | Peytavit et al. | |
| 2007/0117524 | A1* | 5/2007 | Do | H04B 1/44 455/83 |
| 2007/0207747 | A1* | 9/2007 | Johnson | H04B 1/52 455/78 |
| 2007/0262256 | A1* | 11/2007 | Lee | G01J 5/02 250/338.1 |
| 2007/0278407 | A1 | 12/2007 | Wood et al. | |
| 2008/0224071 | A1* | 9/2008 | Kasai | G01N 21/17 250/492.1 |
| 2008/0251870 | A1 | 10/2008 | Morf et al. | |
| 2008/0316087 | A1* | 12/2008 | Stoufer | H04B 17/21 342/169 |
| 2009/0140750 | A1* | 6/2009 | Sugiura | G01R 31/001 324/627 |
| 2010/0223043 | A1* | 9/2010 | Yamagajo | G06F 17/5018 703/14 |
| 2010/0228244 | A1* | 9/2010 | Hancock | A61B 18/1815 606/33 |
| 2010/0245199 | A1* | 9/2010 | Lai | H01Q 1/245 343/787 |
| 2011/0068272 | A1* | 3/2011 | Dupont | G01J 5/20 250/338.4 |
| 2011/0315880 | A1 | 12/2011 | Nemirovsky | |
| 2012/0091342 | A1 | 4/2012 | Berger et al. | |
| 2012/0208008 | A1 | 8/2012 | Tour et al. | |
| 2012/0305808 | A1* | 12/2012 | Zhylkov | H05B 6/6402 250/494.1 |
| 2013/0170690 | A1* | 7/2013 | Backman | H04R 1/028 381/354 |
| 2014/0042324 | A1* | 2/2014 | Kropelnicki | G01J 5/02 250/340 |
| 2014/0203997 | A1* | 7/2014 | Perricone | H01Q 15/14 343/912 |
| 2015/0276489 | A1* | 10/2015 | Cumming | G01J 5/0881 250/338.3 |

OTHER PUBLICATIONS

Demoulin, B., "Electromagnetic Reverberation Chambers" 1st ed., ISBN 978-1-84821-293-0 (2011), Chapter 4, section 4.2 Main Parameters for reverberation chamber design.*

Ansoft, "users guide—High Frequency Structure Simulator", (HFSS) v10, (Jun. 21, 2005) Ansoft Corporation.*

Vitiello, M.S. et al., "Room Temperature Terahertz Detectors based on Semiconductor Nanowire Field Effect Transistors", Proc. SPIE 8268, Quantum Sensing and Nanophotonic Devices IX, 826829, Jan. 20, 2012.

Ouyang, Zhengbiao et al., "A Combined Cavity for High Sensitivity THz Signal Detection", Proceedings of SPIE—The International Society for Optical Engineering, vol. 6840, Nov. 12-14, 2007.

Constantine A. Balanis, "Antenna Theory: Analysis and Design", 2Nd Ed, pp. 513-534, publisher: Wiley India Pvt. Ltd., 2007.

* cited by examiner

METHOD OF SIMULATING THE ABSORPTION OF PLANE WAVES USING FEM SOFTWARE TOOLS

FIELD OF THE INVENTION

The present invention relates to the field of electromagnetic (EM) wave imaging, and more particularly relates to a method of estimating the efficiency of a visualization by detection of EM radiation being irradiated or reflected from objects in the imager's field of view using Finite Element Method (FEM) simulation software tools.

BACKGROUND OF THE INVENTION

Terahertz (THz) radiation imaging is currently an exponentially developing research area with inherent applications such as THz security imaging which can reveal weapons hidden behind clothing from distances of ten meters or more; or medical THz imaging which can reveal, for example, skin cancer tumors hidden behind the skin and perform fully safe dental imaging. Constructing prior art THz detectors is typically a challenging endeavor since both radiation sources and radiation detectors are complex, difficult and expensive to make.

THz radiation is non-ionizing and is therefore fully safe to humans unlike X-ray radiation. THz imaging for security applications, for example, uses passive imaging technology, namely the capabilities of remote THz imaging without using any THz radiation source thus relying solely on the very low power natural THz radiation which is normally emitted from any room temperature body according to well-known black body radiation physics. Passive THz imaging requires extremely sensitive sensors for remote imaging of this very low power radiation. Prior art passive THz imaging utilizes a hybrid technology of superconductor single detectors cooled to a temperature of about 4 degrees Kelvin which leads to extremely complex (e.g., only the tuning of the temperature takes more than 12 hours before any imaging can take place) and expensive (e.g., $100,000 or more) systems.

SUMMARY OF THE INVENTION

The present invention is a method of estimating the efficiency of a visualization by detection of EM radiation being irradiated or reflected from objects in the imager's field of view using Finite Element Method (FEM) simulation software tools. The methodology provides a verification method of antenna operation from an electrical point of view since bolometer performance cannot be estimated using regular antenna parameters such as directivity, gain, impedance matching, etc. as the bolometer does not behave as an antenna but rather behaves as an absorber. An incident wave is triggered on the absorber and the absorption of the bolometer structure is estimated using commercially available Finite Element Method (FEM) software (e.g., ANSYS® HFSS software, CST MICROWAVE STUDIO®, etc.). How much of the energy is reflected is subsequently measured. The energy which is not reflected is considered to be absorbed by the absorber.

There is therefore provided in accordance with the invention, a method of simulating absorption of plane waves using Finite Element Method (FEM) software tools, comprising defining a structure having a single wave-port, placing a bolometer whose absorption is to be simulated within said structure, generating an incident wave excitation by triggering a plane wave utilizing said wave-port, and measuring the power absorbed by said bolometer as a function of total reflected energy.

There is also provided in accordance with the invention, a method of simulating absorption of plane waves using Finite Element Method (FEM) software tools, comprising defining a rectangular simulation volume having six sides, placing a bolometer whose absorption is to be simulated within said simulation volume, generating an incident wave excitation by triggering a plane wave utilizing a wave-port on the top face of said simulation volume, and measuring the power absorbed by said bolometer as a function of total reflected energy.

There is further provided in accordance with the invention, a method of simulating absorption of plane waves using Finite Element Method (FEM) software tools, comprising defining a rectangular simulation volume having first and second opposite faces having perfect magnetic conductor boundary condition, third and fourth opposite faces having perfect electrical conductor boundary conditions, fifth top face wave-port, and a sixth face boundary, placing a bolometer whose absorption is to be simulated within said simulation volume, generating an incident wave excitation by triggering a plane wave utilizing said fifth face wave-port of said simulation volume, and measuring the power absorbed by said bolometer as one minus the total reflected energy.

BRIEF DESCRIPTION OF THE DRAWINGS

The invention is herein described, by way of example only, with reference to the accompanying drawings, wherein.

DETAILED DESCRIPTION OF THE INVENTION

The present invention relates to the field of electromagnetic (EM) wave imaging by estimating the efficiency of visualizing via detection of electromagnetic radiation irradiated or reflected from all objects in the imager's field of view. The detection of electromagnetic waves is achieved using several techniques, e.g., antenna, bolometers, photodiodes, etc. Each detection technique is modeled and designed using a different method, applicable to its physical nature. Antenna are mainly characterized by their far field radiation characteristics (i.e. directivity) and their impedance matching (i.e. realized gain), with modeling performed using 3D electromagnetic solvers for specific excitations. Photodiodes are mainly characterized by their responsivity (i.e. diode current per illumination power) and the diode internal resistivity and capacitance, with their models relying on measurement based equations.

To illustrate the principles of the invention, an example dipole antenna incorporating reflectors and having low thermal mass for detection of Terahertz (THz) radiation is described. The dipole antenna pertains to the field of Terahertz (THz) wave imaging which is the visualization by detection of THz radiation being irradiated or reflected from objects in the imager's field of view. Apart from being a non-ionizing radiation, the wavelengths of the THz portion of the electromagnetic (EM) spectrum are able to penetrate through numerous things such as fog, clothing, packages, etc., enabling imaging with high resolution even by means of relatively small radiating aperture which is crucial in space constrained environments. These qualities make imaging in this part of the electromagnetic spectrum a prime candidate for use in security, surveillance, navigation, etc. systems.

The detection of the THz radiation is typically performed by an antenna with a resistive load, directed at a specific pixel on the body under test. The antenna converts the THz electromagnetic energy into electrical current that heats the resistive load. The temperature change of this resistor is then measured as an indication of the temperature of the body under test.

The dipole antenna enables a bolometer to achieve high sensitivity. In order to achieve high sensitivity, an efficient antenna design is provided which functions to collect the incident electromagnetic energy while at the same time has a very small thermal mass and heat capacitance in order to maximize the resistive element warm-up.

The invention provides a method for designing a microelectromechanical system (MEMS) based dipole antenna with minimal thermal capacitance that, with the aid of reflectors, forms a directive antenna.

Sensors at THz frequencies are typically bolometers, since electronics cannot reach these frequencies. Bolometers can be implemented using slightly modified CMOS techniques or using a CMOS SOI process with MEMS post processing. A THz sensor can be directly integrated with readout circuitry in a CMOS-SOI process. One sensor that can be used is an antenna coupled bolometer.

In one embodiment, a broadband antenna with a large thermal capacitance is connected to a load impedance (i.e. termination resistor or port) by a capacitive coupling through a vacuum gap. This physical separation provides thermal isolation to the resistor, which heats up considerably due to the low thermal capacitance. The THz sensor is realized with a temperature dependent resistor or with a FET where it's strongly temperature dependent subthreshold current is used as a sensor.

A bolometer based detector may take the form of a lens on the top of the structure to collect the incident electromagnetic energy of individual pixels. Each pixel is adapted to be thermally isolated from other pixels and from the entire structure. This is achieved by creating a vacuum around the bolometers. In order to increase the sensitivity of the bolometer, the noise is reduced by cooling the entire structure and the antenna down to cryogenic temperatures.

In one embodiment, a basic pixel can take the form of a spiral shaped antenna which performs well and has a wide bandwidth. The antenna is directly connected to a bolometer, which in this example embodiment, is a resistive gate Field-Effect-Transistor (FET). The temperature change of the transistor is sampled through the change in the transistor's current. The antenna and bolometer are separated from the rest of the structure using MEMS techniques to obtain the thermal isolation.

In another embodiment, the pixel is implemented using MEMS technology where the metal antenna is replaced with a high resistance antenna. In this embodiment, the antenna does not have a resistive port and the heating is due to the currents in the antenna itself. The MEMS process separates the antenna from the rest of the structure and thus reduces its thermal capacitance and thermal conductivity to the heat sink such that its temperature change is larger. From an electrical point of view, the best way to absorb power is to use a high effective area antenna coupled to a perfectly matched port. The use of an antenna shaped resistive material, however, results in performance far from optimal.

In another embodiment, a suspended antenna and bolometer are constructed over a semiconductor substrate. This embodiment allows for thermal isolation of the bolometer without having to isolate it from the antenna by means of electrical capacitance. The antenna may comprise the well-known dipole antenna or double dipole antenna which has low thermal mass but exhibits poor electrical performance due to its narrow bandwidth.

In another detector embodiment, the antenna is directly connected to the termination resistor (i.e. load impedance) while the combined thermal capacitance of the antenna remains low. A large thermal capacitance, combined with low thermal conductivity, inevitably results in long thermal time constants and hence in low frame rates for thermal sensors.

Figure 1:
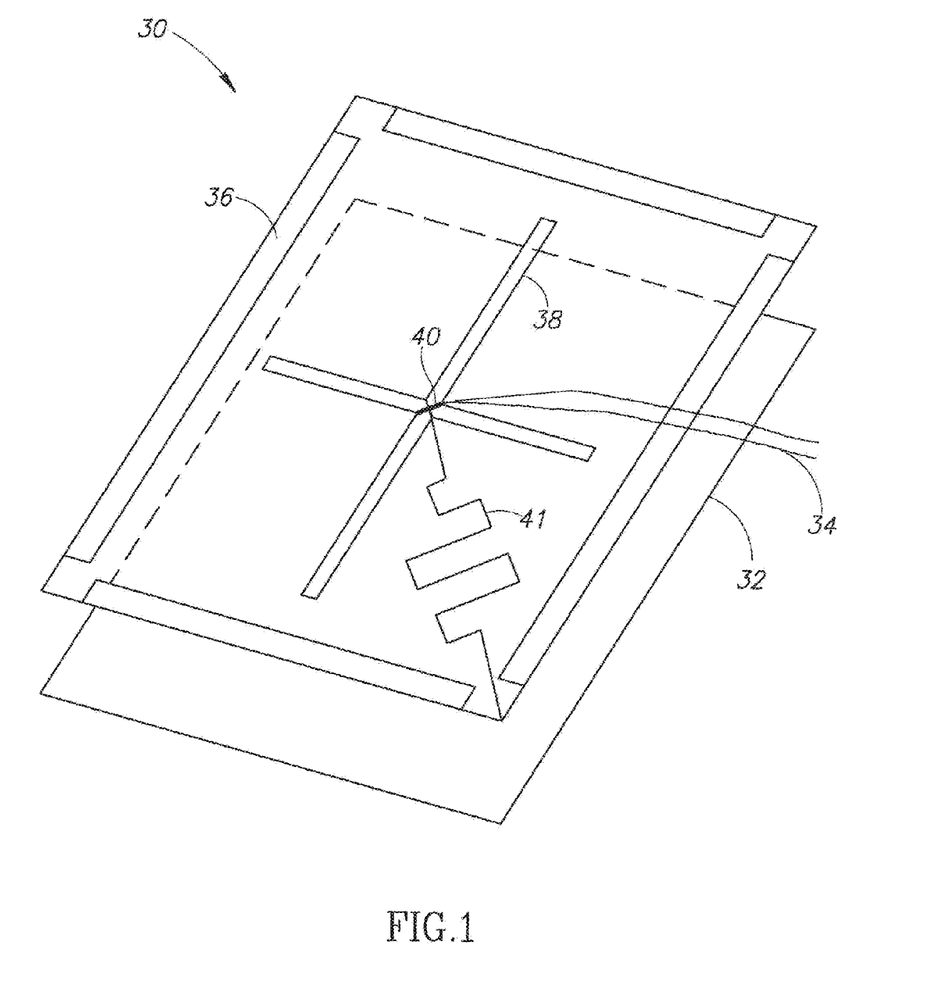
FIG. 1 is a diagram illustrating an example embodiment of a pair of folded dipoles connected to a single load impedance.

The example antenna of FIG. 1 provides a structure that exhibits both low thermal capacitance and high electrical performance while provides superior performance. The antenna is suitable for implementation in numerous detectors, as well as in any application that requires a low thermal mass. The antenna structure is small in terms of heat capacitance, but at the same time it has high volume from an electrical perspective. In one embodiment, the antenna comprises a standard dipole with two arms having minimal metal widths.

In order to direct the Terahertz radiation in the Z direction without increasing the antenna thermal capacitance, a plurality of reflectors is used that do not physically touch the antenna itself. In one example embodiment, three reflectors are used. The first reflector is a conducting plane located substantially $\lambda/4$ below the dipole, where $\lambda$ is the wavelength. This reflector prevents energy radiation in the negative Z direction. The second and the third reflectors are located in the same plane as the dipole (i.e. in the Z=0 plane). These two reflectors are spaced apart parallel to the dipole and function in the same manner as well-known Yagi-Uda reflectors. Yagi-Uda antennas are directional along the axis perpendicular to the dipole in the plane of the elements, from the reflector toward the driven element and the one or more directors. By placing the two reflectors on the two sides of the dipole and at equal distances, they prevent energy radiation in the +X and the −X direction. These three reflectors (i.e. a conducting plane and two Yagi-Uda reflectors) direct the electromagnetic radiation in the +Z direction and since they do not have mechanical connection to the dipole itself, they do not increase the thermal capacitance of the antenna.

A diagram illustrating an example embodiment of a pair of folded dipoles connected to a single load impedance is shown in FIG. 1. The antenna, generally referenced 30, comprises a pair of folded dipoles 38 connected to a single load impedance 40 and suspended by holding arm 41, an infinite conductive plane reflector 32 located λ/4 below the dipole, two pairs of Yagi-Uda reflectors 36 and readout circuit lines 34.

In this embodiment, the two folded dipole elements are connected to a single resistive element. In this configuration, the current flows through the resister in any polarization, but will not flow through the perpendicular dipole structure.

Bolometers are mainly characterized by their temperature rise relative to incident electromagnetic power at a certain frequency. This parameter is set by several parameters such as the absorption (i.e. the portion of the incident power that turns into heat) and the thermal capacitance and thermal conductivity of the bolometer to the heat sink. In order to determine the absorption a 3D electromagnetic simulation is performed that mimics the incident power excitation and is capable of measuring the absorbed power.

One technique of modeling the bolometer absorption quality is to use Floquet port excitation which is implemented in commercially available 3D electromagnetic simulators such as ANSYS® HFSS software, CST MICROWAVE STUDIO® software, etc. This method assumes an infinite periodic structure of unit cells (mostly used for antenna array), where Floquet boundary conditions are set on each unit, i.e. electromagnetic power (Poynting vector) exiting one face of the unit, must be compensated by electromagnetic power entering from the opposite face at the same value, but possibly having different phase. These assumptions are very good for an infinite periodic structure but are not valid for a single absorber or even a finite array.

A Floquet port excitation example is provided below. In this example, the simulator volume and sample bolometer were subject to high frequency structural simulator (HFSS) simulation. The top and bottom surfaces of the simulator volume are defined as Floquet ports that represent incident and reflected plane waves with different propagation direction as a function of azimuth (phi) and elevation (theta) angles. The matching periodical boundary conditions are assigned for side surfaces that extend the model periodically to infinity in both directions. The results of such HFSS simulations are valid if the bolometer antenna surface is much larger than the wavelength of incident plane wave. Note that it is customary to consider two polarization cases of plane waves obliquely incident on planar surfaces: (1) plane waves with an electrical vector perpendicular to plane of incidence (i.e. TEM 00 mode); and (2) plane waves with electrical vector parallel to plane of incidence (i.e. TEM 00 mode). The plane of incidence is defined as a plane normal to the antenna that contains the direction of propagation of the incident wave.

Considering the results of HFSS simulation for the reflection coefficient in TEM 00 mode, the electrical vector of TEM 00 incident plane wave is parallel to the antenna surface for any angle of incident. Thus, the scattered back energy should be less than the energy scattered back in TEM 00 mode.

Another technique of modeling the bolometer absorption quality is to excite a free space plane wave with a known power and subsequently calculate the dissipated power on the absorber. The ratio between the absorbed power and the incident power is then calculated. Two potential problems with this technique are: (1) since the plane wave excitation in free space is diffracted, not all the excited power arrives to the absorber as a plane wave; and (2) since the excited plane wave power cannot be set in some simulators (ANSYS HFSS, for example), the user is forced to estimate it by a separate simulation.

In another embodiment, an alternative absorber estimation methodology is described. More specifically, the methodology provides a verification method of antenna operation from an electrical point of view. It is noted that bolometer performance cannot be estimated solely based on regular antenna parameters such as directivity, gain, impedance matching, etc. as the bolometer does not behave as an antenna but rather behaves as an absorber. This can be explained by the following two examples:

1. In antenna theory, the ohmic loss on the metal arms of an antenna is considered to be harmful as it reduces the amount of the power which is emitted/received by the source. In the case of a detector comprising a bolometer and related antenna, any absorbed power (either in the resistor or in the antenna arms) contributes to heating the entire structure and thus is considered helpful.
2. According to well-known antenna theory, mismatch in impedance results in energy reflection from the antenna/port which decreases the antenna efficiency by the reflection coefficient. Apart from that, energy reflected from the antenna to the transmitter might harm the transmitter itself, and in receiving mode might cause a problem of cross coupling with an adjacent antenna. For this reason, in most cases, there are strict demands on the antenna impedance matching on specific bandwidths. For example, a dipole antenna at resonance frequency requires a 75Ω impedance for perfect matching. In the case of an antenna based bolometer, impedance mismatch reduces the amount of absorbed energy at the resonance frequencies, but sometimes will increase the absorbed energy on other frequencies. Since the critical parameter for bolometers is the total absorbed energy, integrated over all a wide bandwidth, sometimes the optimal design is a non-matched impedance.

To estimate the absorption of the bolometer structure using commercially available Finite Element Method (FEM) software (e.g., ANSYS® HFSS software, CST MICROWAVE STUDIO®, etc.) there is a need to trigger an incident wave on the absorber and subsequently measure how much of the energy is reflected. The energy which is not reflected must be absorbed by the absorber. The following description uses HFSS terminology as an example but is applicable to other full wave FEM simulation software tools.

Figure 2:
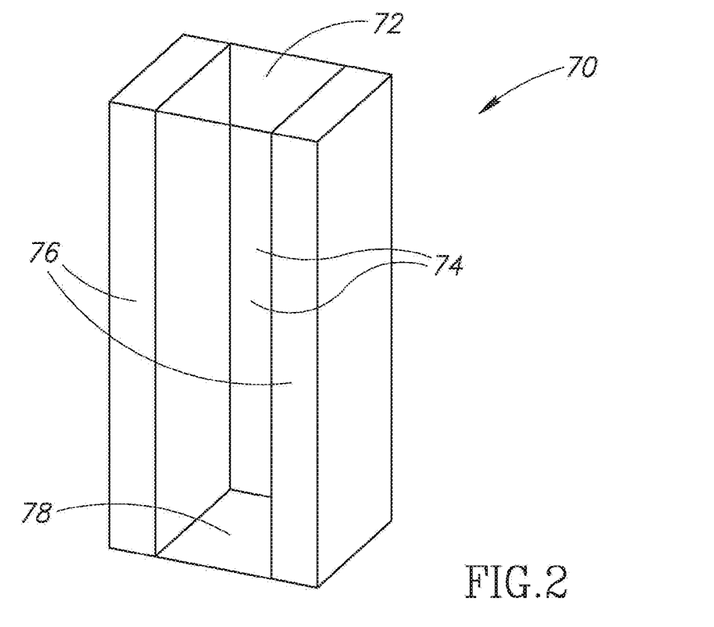
FIG. 2 is a diagram illustrating an example simulation volume.

For the incident wave excitation, it is preferable to trigger a plane wave by using a wave-port, while the entire structure is defined with no other ports. By using a wave-port it is relatively easy to calculate the total reflected energy from the scattering parameters. The total absorbed energy is one minus the reflected energy. In order to generate and propagate a plane wave by a wave-port in a manner that will not induce diffraction and wave-guide modes of all kinds, the entire structure is confined inside a rectangular simulation volume having a dielectric material inside it, that suits the problem at hand. A diagram illustrating an example simulation volume having a vacuum inside it, generally referenced 70, is shown in FIG. 2. Two opposite faces 74 of the volume have perfectly magnetic conductor boundary conditions, while the other two opposite faces 76 are covered by a perfect conductor. The wave-port is defined on the fifth face 72. The sixth face 78 boundary is defined using one of the following methods, as it is applicable to the particular implementation: (1) a perfectly magnetic conductor; (2) a perfectly electric conductor; (3) a wave-port; and (4) any other boundary condition in which the energy can be absorbed or escape, while it can be calculated by the field calculator.

Figure 3:
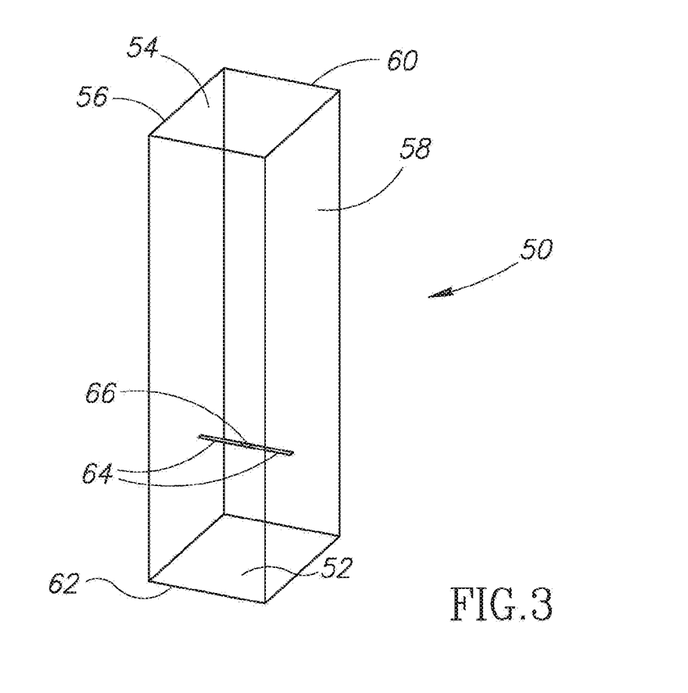
FIG. 3 is a diagram illustrating an example bolometer inside a simulation volume.

A diagram illustrating an example bolometer inside a simulation volume is shown in FIG. 3. The simulation volume, generally referenced 50, comprises an empty cube having six sides including (1) two opposite faces 56, 58 set as perfect electrical conductors (the electrical field must be normal to these faces); (2) two opposite faces 52, 60 set as perfect magnetic conductors (the magnetic field must be normal to these faces); (3) a top face 54 on which is placed a port (i.e. a wave-port) used by the simulator for generating the electromagnetic energy and also capable of calculating the energy flowing through it; and (4) a bottom face 62 which can have several types of boundary conditions as long as the electromagnetic energy cannot escape through it without being calculated. A first option for the bottom face is a port whereby the total energy going through the port will be accounted for in terms of S-parameters. A second option for the bottom face is a perfect E/H conductor that would prevent power flow (no energy flows through the port and the energy is reflected back up the simulation volume). The simulation volume uses a perfect E conductor. Note that the ground conductor under the antenna arms is an E conductor.

The bolometer (i.e. metal antenna arms 64 and resistor 66) is placed inside the simulation volume. In case the bolometer has additional components (e.g., dielectric material for holding arms, read out lines, etc.) that affect its electrical performance, they should also be incorporated within the simulation volume.

Figure 4:
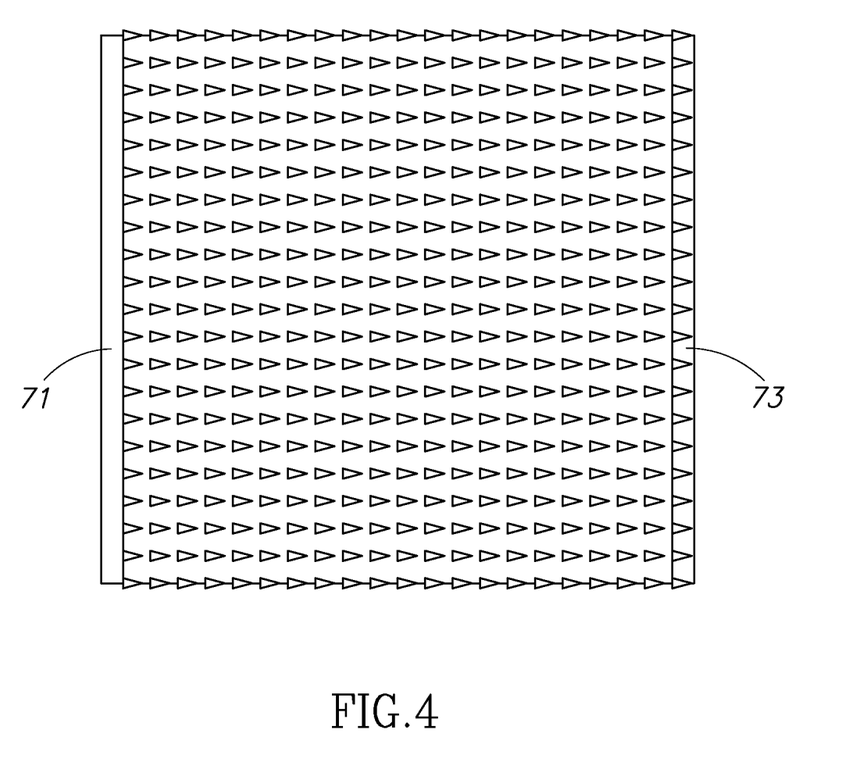
FIG. 4 is a diagram illustrating a top view of an example transverse electromagnetic (TEM) mode.
Figure 5:
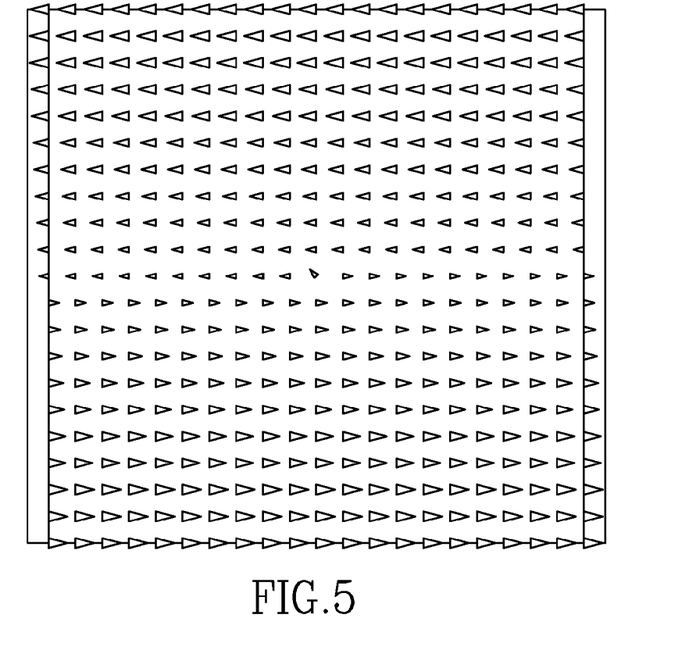
FIG. 5 is a diagram illustrating a top view of a first example transverse electromagnetic odd mode.

A diagram illustrating a top view of an example transverse electromagnetic (TEM) mode is shown in FIG. 4. The transverse electromagnetic (TEM) mode (mode 00) is shown which is used to generate the plane wave in the empty simulation volume. The tiny arrows represents the vector electric field. The left and right E walls 71, 73 are shown while the top and bottom H walls are not shown. The bottom face comprises a perfect electrical conductor.

Figure 9A:
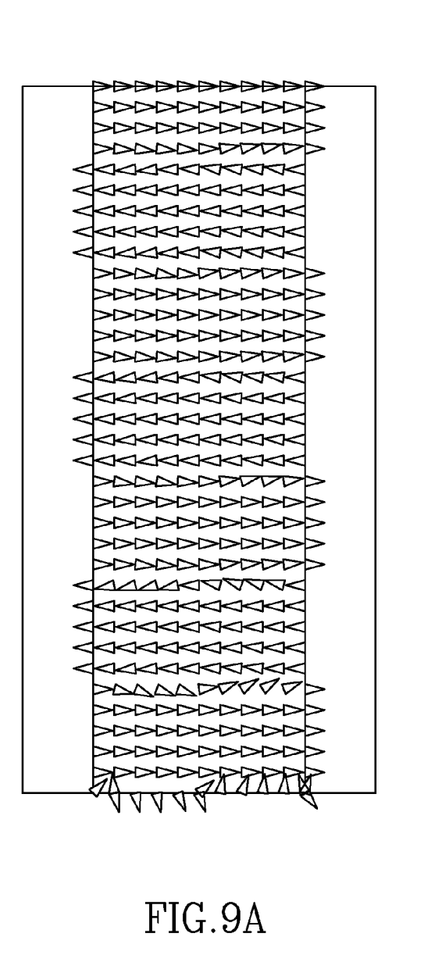
FIG. 9A is a diagram illustrating a side view of an example transverse electromagnetic mode forming a plane wave with a zero degree phase.
Figure 9B:
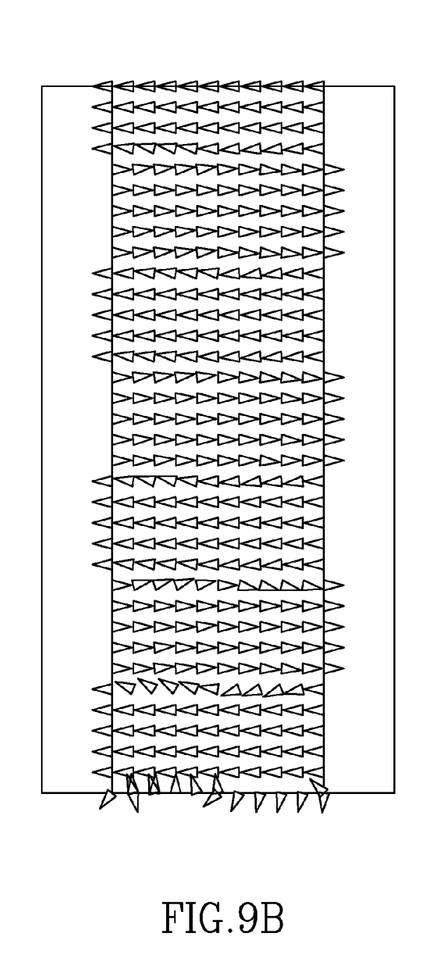
FIG. 9B is a diagram illustrating a side view of an example transverse electromagnetic mode forming a plane wave with a 180 degree phase.

A diagram illustrating a side view of an example transverse electromagnetic mode forming a plane wave with a zero degree phase is shown in FIG. 9A. A diagram illustrating a side view of an example transverse electromagnetic mode forming a plane wave with a 180 degree phase is shown in FIG. 9B. The simulation volume setup in FIGS. 2 and 3 can trigger and support plane waves regardless of the excitation frequency and/or the unit size, as can be seen in FIGS. 9A and 9B.

Figure 6:
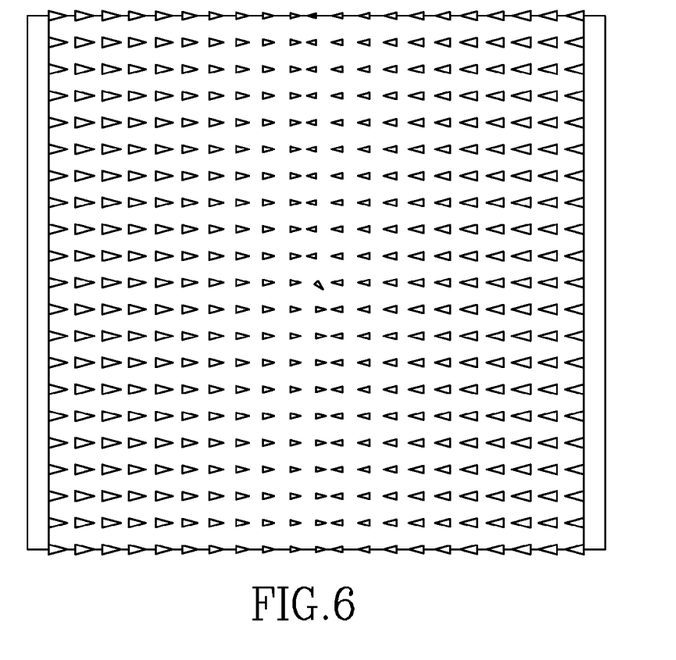
FIG. 6 is a diagram illustrating a top view of a second example transverse electromagnetic odd mode.

A diagram illustrating a top view of a first example transverse electromagnetic odd mode is shown in FIG. 6. The left and right walls comprise the perfect E walls while the top and bottom comprise H walls. Transverse Electric (TE) odd mode 10 has one null in the center of the wave port as depicted by the tiny arrows running horizontally.

A diagram illustrating a top view of a second example transverse electromagnetic odd mode is shown in FIG. 6. The left and right walls comprise the perfect E walls while the top and bottom comprise H walls. TE odd mode 01 has one null in the center of the wave port as depicted by the tiny arrows running vertically.

Figure 7:
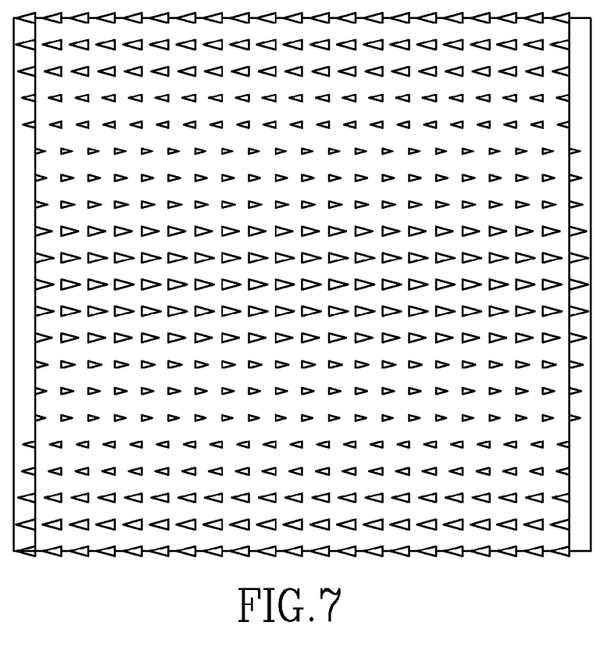
FIG. 7 is a diagram illustrating a top view of a first example transverse electromagnetic even mode.

A diagram illustrating a top view of a first example transverse electromagnetic even mode is shown in FIG. 7. The left and right walls comprise the perfect E walls while the top and bottom comprise H walls. TE even mode 20 has two nulls as depicted by the tiny arrows running horizontally approximately one quarter down from the top and one quarter up from the bottom of the simulation volume.

Figure 8:
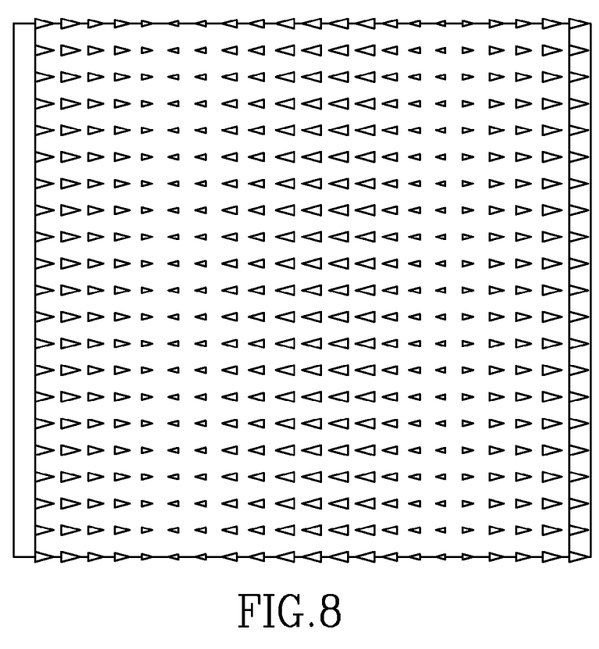
FIG. 8 is a diagram illustrating a top view of a second example transverse electromagnetic even mode.

A diagram illustrating a top view of a second example transverse electromagnetic even mode is shown in FIG. 8. The left and right walls comprise the perfect E walls while the top and bottom comprise H walls. TE even mode 02 has two nulls as depicted by the tiny arrows running vertically approximately one quarter in from the left and one quarter in from the right wall of the simulation volume.

In each of the various TE modes (e.g., shown in FIGS. 5-8), the total absorption can be calculated as one minus the total scattering energy from the TEM mode to all the other existing modes as expressed below.

$$\text{Absorption} = 1 - \Sigma_{nm} |S_{00 \to nm}|^2 \quad (1)$$

Where nm represents the different possible TE modes. $S_{00 \to nm}$ represent the scattering parameters between the TEM mode 00 and the TE mode nm.

In order to measure how much power is absorbed in a body under a plane wave excitation, such a body is placed inside a structure such as in FIGS. 2 and 3. The plane wave excites currents on the body which in turn cause the plane wave to be partially absorbed. The part which is not absorbed is scatted in all directions, according to the absorber shape. The scattered electromagnetic fields are mathematically represented by a linear composition of all the waveguide modes, so that one must calculate all those modes on the port. The absorption is calculated by the scattering parameters of the port, as one minus the reflection coefficients between the lowest mode (i.e. the plane wave) and all the other modes as shown in Equation 1 above.

Figure 10:
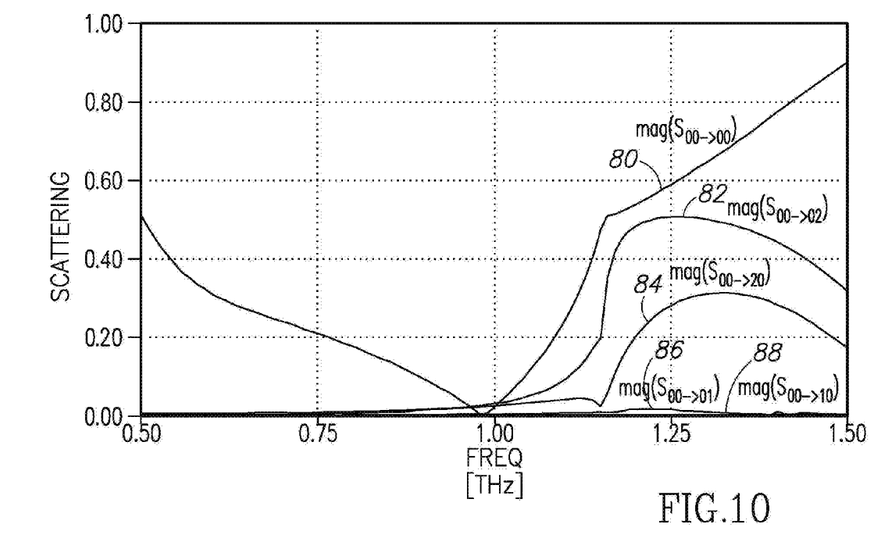
FIG. 10 is a graph illustrating an example of scattering parameters for different modes.

A graph illustrating an example of scattering parameters (magnitude) for different modes is shown in FIG. 10. The TEM mode 00 is generated and hits the bolometer and scatters into the simulation volume. The graph illustrates the electromagnetic field distribution caused by the scattering and represents a linear composition series of electromagnetic functions. The Y-axis shows the degree of scattering with zero representing no scattering from the TEM mode 00 to the suitable TE mode nm, and one representing total scattering. A lower scattering number is better in terms of absorption. Traces 80, 82, 84, 86, 88 represent the magnitude of the scattering for various TE modes.

Figure 11:
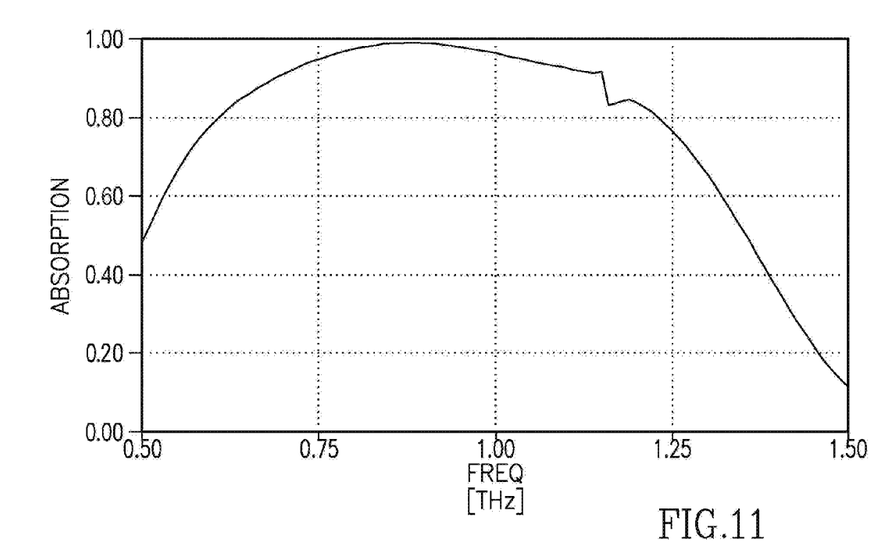
FIG. 11 is a graph illustrating an example of absorption for the scattering parameters of FIG. 10.

A graph illustrating an example of absorption for the scattering parameters of FIG. 10 is shown in FIG. 11. The Y axis in this graph is absorption (and not scattering) with zero representing no absorption and total scattering and one representing total absorption. This graph represents one minus the sum of the scattering of the series shown in FIG. 10. Note that in this example relatively good absorption is obtained in the desired frequency range of approximately 0.8-1.0 THz.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A computer-implemented method of simulating absorption of plane waves using Finite Element Method (FEM) software tools, comprising:
    defining a simulation in the Finite Element Method software tools of a structure having a single wave-port, wherein said structure comprises at least one of a pair of opposite faces having perfect magnetic conductor boundary conditions and a pair of opposite faces having perfect electrical conductor boundary conditions;
    placing a simulation in the Finite Element Method software tools of a physical bolometer whose absorption is to be simulated within said structure, said bolometer having a physical structure comprising an antenna and a resistive load;
    generating a simulation in the Finite Element Method software tools of an incident wave excitation by triggering a plane wave utilizing said wave-port;
    determining power absorbed by said physical bolometer as a function only of total reflected energy based on results of the simulation in the Finite Element Method software tools; and
    verifying operation of the physical bolometer based on the determined power.

2. The method according to claim 1, wherein said structure comprises a rectangular simulation volume having a vacuum therein.

3. The method according to claim 1, wherein said structure comprises first and second opposite faces having perfect magnetic conductor boundary conditions.

4. The method according to claim 1, wherein said structure comprises third and fourth opposite faces having perfect electrical conductor boundary conditions.

5. The method according to claim 1, wherein said structure comprises a bottom face perfect magnetic conductor.

6. The method according to claim 1, wherein said structure comprises a bottom face perfect electrical conductor.

7. The method according to claim 1, wherein said structure comprises a bottom face wave-port.

8. The method according to claim 1, wherein said structure comprises a bottom face having a boundary condition in which the energy can be absorbed or escape while the energy can be calculated by the field calculator component of said software tool.

9. The method according to claim 1, wherein the total absorbed power is one minus the total reflected energy.

10. The method according to claim 1, wherein scattered electromagnetic fields are mathematically represented by one or more waveguide modes.

11. The method according to claim 1, wherein power absorbed is calculated using the equation Absorption=$1-\Sigma_{nm}|S_{00->nm}|^2$ where nm represents different possible transverse electric modes and $S_{00->nm}$ represents scattering parameters between a transverse electromagnetic mode 00 and a transverse electric mode nm.

12. A computer-implemented method of simulating absorption of plane waves using Finite Element Method (FEM) software tools, comprising:
    defining a rectangular simulation volume having six faces in the Finite Element Method software tools, wherein said rectangular simulation volume comprises at least one of a pair of opposite faces having perfect magnetic conductor boundary conditions and a pair of opposite faces having perfect electrical conductor boundary conditions;
    placing a simulation in the Finite Element Method software tools of a physical bolometer whose absorption is to be simulated within said simulation volume, said bolometer having a physical structure comprising an antenna and a resistive load;
    generating a simulation in the Finite Element Method software tools of an incident wave excitation by triggering a plane wave utilizing a wave-port on a top face of said simulation volume; and
    determining power absorbed by said physical bolometer as a function only of total reflected energy based on results of the simulation in the Finite Element Method software tools; and
    verifying operation of the physical bolometer based on the determined power.

13. The method according to claim 12, wherein said simulation volume comprises first and second opposite faces having perfect magnetic conductor boundary conditions.

14. The method according to claim 12, wherein said simulation volume comprises third and fourth opposite faces having perfect electrical conductor boundary conditions.

15. The method according to claim 12, wherein said simulation volume comprises a sixth bottom face perfect magnetic conductor.

16. The method according to claim 12, wherein said simulation volume comprises a sixth bottom face perfect electrical conductor.

17. The method according to claim 12, wherein said simulation volume comprises a sixth bottom face wave-port.

18. The method according to claim 12, wherein said simulation volume comprises a sixth bottom face having a boundary condition in which the energy can be absorbed or escape while the energy can be calculated by a field calculator component of said software tool.

19. The method according to claim 12, wherein the total absorbed power is one minus the total reflected energy.

20. The method according to claim 12, wherein scattered electromagnetic fields are mathematically represented by one or more waveguide modes.

21. The method according to claim 12, wherein the power absorbed is calculated using the equation Absorption=$1-\Sigma_{nm}|S_{00->nm}|^2$ where nm represents different possible transverse electric modes and $S_{00->nm}$ represent scattering parameters between a transverse electromagnetic mode 00 and a transverse electric mode nm.

22. A computer-implemented method of simulating absorption of plane waves using Finite Element Method (FEM) software tools, comprising:
    defining a rectangular simulation volume having first and second opposite faces having perfect magnetic conductor boundary conditions, third and fourth opposite faces having perfect electrical conductor boundary conditions, a fifth top face wave-port, and a sixth face boundary;

placing a simulation of a physical bolometer whose absorption is to be simulated within said simulation volume, said bolometer having a physical structure comprising an antenna and a resistive load;

generating a simulation of an incident wave excitation by triggering a plane wave utilizing said fifth face wave-port of said simulation volume; and determining the power absorbed by said physical bolometer as one minus the total reflected energy based on results of the simulation.

23. The method according to claim 22, wherein scattered electromagnetic fields are mathematically represented by one or more waveguide modes.

24. The method according to claim 22, wherein the power absorbed is calculated using the equation Absorption=1−$\Sigma_{nm}|S_{00->nm}|^2$ where nm represents different possible transverse electric modes and $S_{00->nm}$ represent scattering parameters between a transverse electromagnetic mode 00 and a transverse electric mode nm.

* * * * *